United States Patent
Li et al.

(10) Patent No.: US 11,786,322 B2
(45) Date of Patent: Oct. 17, 2023

(54) DIAGNOSIS AND TREATMENT INTEGRATED SOFT MEDICAL ROBOT FOR GASTROINTESTINAL ENDOSCOPY

(71) Applicant: Harbin Institute of Technology, Harbin (CN)

(72) Inventors: Longqiu Li, Harbin (CN); Dekai Zhou, Harbin (CN); Yongchang Zhang, Harbin (CN); Pengchun Li, Harbin (CN); Jiale Quan, Harbin (CN); Xiaocong Chang, Harbin (CN); Guangbin Shao, Harbin (CN)

(73) Assignee: HARBIN INSTITUTE OF TECHNOLOGY, Harbin (CN)

( * ) Notice: Subject to any disclaimer, the term of this patent is extended or adjusted under 35 U.S.C. 154(b) by 311 days.

(21) Appl. No.: 17/383,498

(22) Filed: Jul. 23, 2021

(65) Prior Publication Data
US 2022/0409305 A1 Dec. 29, 2022

(30) Foreign Application Priority Data
Jun. 24, 2021 (CN) .......................... 202110705249.2

(51) Int. Cl.
*A61B 1/00* (2006.01)
*A61B 34/30* (2016.01)
(Continued)

(52) U.S. Cl.
CPC .............. *A61B 34/30* (2016.02); *A61B 1/273* (2013.01); *A61B 90/30* (2016.02); *A61B 90/361* (2016.02);
(Continued)

(58) Field of Classification Search
CPC ....... A61B 1/05; A61B 1/00071; A61B 1/273; A61B 90/30; A61B 1/0055; A61B 1/2736;
(Continued)

(56) References Cited

U.S. PATENT DOCUMENTS 6,226,933 B1 * 5/2001 Nelson .................... E04H 12/20
43/124
2011/0295065 A1 * 12/2011 Gurusamy ........... A61B 1/0057
600/141

(Continued)

*Primary Examiner* — Anh Tuan T Nguyen
*Assistant Examiner* — Sung Ham
(74) *Attorney, Agent, or Firm* — IPRO, PLLC; Na Xu

(57) ABSTRACT

The disclosure provides a diagnosis and treatment integrated soft medical robot for gastrointestinal endoscopy, including a robot body, a camera, illumination devices, a flexible dielectric elastomer actuator, air cylinders, linear motors, a controller and external hoses. The robot body is a multi-channel hose, and includes a central channel and circumferential channels, the central channel is configured to accommodate conducting wires and signal wires, the circumferential channels include at least three microfluid channels. The linear motors control fluid pressures in the microfluid channels by driving piston rods of the air cylinders so that the robot body steers through being driven by fluid. The camera performs real-time image acquisition. The controller controls the flexible dielectric elastomer actuator to capture a target. The disclosure realizes the real-time image acquisition on a digestive tract, particularly a lesion, and can integrally and fast complete diagnosis and treatment.

9 Claims, 5 Drawing Sheets

(51) Int. Cl.
    *A61B 90/30*     (2016.01)
    *A61B 90/00*     (2016.01)
    *A61B 1/273*     (2006.01)

(52) U.S. Cl.
    CPC . *A61B 2034/301* (2016.02); *A61B 2562/0285* (2013.01); *A61B 2562/162* (2013.01)

(58) Field of Classification Search
    CPC ..... A61B 90/361; A61B 1/0052; A61B 34/30; A61B 1/00006; A61B 1/0051; A61B 1/0676; A61B 1/00087; A61B 1/00114; A61B 2034/301; A61B 2562/0285; A61B 2562/162; A61B 2090/065
    See application file for complete search history.

(56) References Cited

U.S. PATENT DOCUMENTS

| | | | |
|---|---|---|---|
| 2012/0035416 A1* | 2/2012 | Fernandez | A61B 1/00149 600/102 |
| 2019/0159662 A1* | 5/2019 | Papas | A61B 1/00032 |
| 2022/0039784 A1* | 2/2022 | Hwang | A61M 25/0155 |

* cited by examiner

DIAGNOSIS AND TREATMENT INTEGRATED SOFT MEDICAL ROBOT FOR GASTROINTESTINAL ENDOSCOPY

TECHNICAL FIELD

The disclosure belongs to the technical field of medical diagnosis and treatment, and particularly relates to a diagnosis and treatment integrated soft medical robot for gastrointestinal endoscopy.

BACKGROUND

Gastrointestinal calculus is a common digestive system disease, which is mostly caused by coagulation of some ingested plant ingredients or swallowed hair or some minerals such as calcium carbonate, barium-containing drugs, bismuth-containing drugs in the intestines and stomach. The gastrointestinal calculus is mostly difficult to be excreted, and often causes symptoms such as upper abdominal discomfort, anorexia or different degrees of abdominal pain and bloating. The diseases such as ulcer or perforation may occur after long-term stimulation on the gastrointestinal parts, so that great adverse influence is caused on the health status and the life quality of patients.

Existing gastrointestinal calculus treatments include oral drug dissolution, extracorporeal shock wave crushing, net sleeve lithotripsy under X-rays, biopsy forceps cutting under a microscope and surgery. The oral drug dissolution method has a long treatment period and great injury to the inner walls of intestine and stomach. The extracorporeal shock wave crushing method is not applicable to hair calculi, shellac calculi, etc. The net sleeve lithotripsy under X-rays needs repeated cutting on the calculi, and the calculi are excreted with the help of drugs. The operation precision of this method is low, and the inner wall of the digestive tract is easy to be injured in the operation process. Similar, the biopsy forceps cutting method under a microscope is also easy to stimulate and injure the inner wall of the digestive tract. The surgery causes great injury on tissues and organs and requires a long recovery period. At present, in the diagnosis and treatment processes of the gastrointestinal calculus, the diagnosis and treatment are mostly separated, current treatment methods have problems such as long treatment period, certain injury to the digestive tract of a patient, unclear treatment effect. At the same time, these methods often bring some side effects, such as nausea, vomiting, respiratory depression, and decreased heart rate. There are few reports about a soft medical robot with good biocompatibility being able to acquire images of the digestive tract in real time, and provided with a front-end actuator and realizing diagnosis and treatment integration.

Based on the above, there is an urgent need of providing a diagnosis and treatment integrated soft medical robot realizing real-time image acquisition and provided with a front-end actuator, to solve the problems above.

SUMMARY

The disclosure aims at presenting a diagnosis and treatment integrated soft medical robot for gastrointestinal endoscopy to achieve the real-time image acquisition of the digestive tract, particularly the lesions. The diagnosis and treatment process can be integrally and quickly completed. The robot can be used for diagnosis and treatment on diseases such as gastrointestinal calculus and gastrointestinal polyposis. Compared with other therapies, this therapy can reduce the damage to the digestive tract and shorten the treatment cycle.

In order to achieve the objectives above, the technical solution of the disclosure is achieved in such a way:

A diagnosis and treatment integrated soft medical robot for gastrointestinal endoscopy includes a robot body, a camera, illumination devices, a flexible dielectric elastomer actuator, air cylinders, linear motors, a controller and external hoses. The robot body is a multichannel hose, and includes a central channel and circumferential channels. The central channel is configured to accommodate conducting wires and signal wires. The circumferential channels include at least three microfluid channels. The front end of each microfluid channels is a sealed end. The rear end of each microfluid channels is an open end. The open end of each microfluid channels is communicated with the flow channel port of an air cylinder.

The camera is disposed at a front end of the central channel of the robot body. A plurality of illumination devices are distributed around the camera.

The flexible dielectric elastomer actuator is fixedly connected to the front end of the robot body. The air cylinders, the linear motors and the controller are all disposed at the rear end of the robot body. Each of the microfluid channels is correspondingly disposed with one air cylinder. Each of the air cylinders corresponds to one linear motor. Each of the microfluid channels and the corresponding air cylinder are connected through an external hose, the piston rod of the air cylinders is connected with a shaft of the corresponding linear motor through a coupling. The conducting wires and signal wires of the camera, the flexible dielectric elastomer actuator are all connected with the controller. The linear motors control fluid pressures in the corresponding microfluid channels by driving the piston rods of the corresponding air cylinders so that the robot body steers through being driven by fluid. At the same time, the camera performs real-time image acquisition, and the controller controls the flexible dielectric elastomer actuator to capture a target.

Further, the robot body includes three microfluid channels, additionally, the three microfluid channels are uniformly distributed in a circumferential direction. The inner wall of a front section portion of each of the microfluid channels adopts lattice structures as robot body front end lattice microfluid channels. The inner wall of other portions of the microfluid channels is of a smooth structure as a robot body smooth microfluid channel.

Further, the flexible dielectric elastomer actuator includes a flexible dielectric elastomer actuator framework and three dielectric elastomer driving units. The flexible dielectric elastomer actuator framework includes a framework main body and three capture arms. The three capture arms are uniformly disposed on the periphery of the framework main body. Every dielectric elastomer driving unit is pasted to an inner side of each of the capture arms. The three capture arms are folded to be in a gathered state. Every dielectric elastomer driving units includes a first encapsulation protection layer, a first sensing layer, a second sensing layer, a second encapsulation protection layer, a first flexible electrode layer, a dielectric elastomer layer, a second flexible electrode layer and a third encapsulation protection layer sequentially disposed from inside to outside. The area of the dielectric elastomer layer can be expanded or contracted by adjusting the driving voltage, so that the flexible dielectric elastomer actuator can be driven to complete an opening or closing action, so as to achieve the capture on the target.

Further, the framework main body is of a regular triangular structure. A center through hole allowing the camera to pass and to be fixed is provided in the center of the framework main body. The capture arms are of a hexagonal structure, and a hexagonal through hole is provided in a middle portion of every capture arm.

Further, a layer of fiber woven mesh is embedded in an outer layer of the robot body.

Further, bristle-like locking structures are provided at front ends of the capture arms.

Further, the first sensing layer, the second sensing layer, the first encapsulation protection layer and the second encapsulation protection layer are combined into a flexible tactile sensor.

Further, the sensing layer is a thin film with surface micro-nano structure made of carbon nano material or metal nano material.

Further, a material of the encapsulation protection layer is polydimethylsiloxane.

Further, a material of the robot body is silicone rubber, and a material of the flexible dielectric elastomer actuator framework is polyvinyl chloride.

Compared with the prior art, the diagnosis and treatment integrated soft medical robot for gastrointestinal endoscopy of the disclosure has the following advantages:
1. The design of integrated camera and flexible actuator makes the robot complete the diagnosis and treatment process in one step and shorten the diagnosis and treatment cycle.
2. The main body and actuator of the robot are manufactured by soft materials with good biocompatibility, so the injury to the digestive system, particularly to the inner wall of the digestive tract can be reduced.
3. The camera and the illumination devices are embedded in the central channel inside the robot body. The state of the inner wall of the digestive track and the front-end actuator can be monitored in real time.
4. The robot body is provided with three microfluid channels uniformly distributed in the circumferential direction. The front end is of lattice structures, a pressure difference is generated among the three microfluid channels driven by fluid, its front end can be turned 360° steering, so the robot can be guide in the cavity of complicated three-dimensional digestive system can be realized.
5. The outer layer of the robot body is embedded with fiber woven mesh, which is used to limit circumferential deformation, prevent damage to the inner wall of digestive tract, and transfer fluid driving energy to bending deformation.
6. The front end of the robot body is carried with a flexible dielectric elastomer actuator. The actuator has high control precision and fast response speed, which can achieve precision operations such as gastrointestinal calculus capture and gastrointestinal polyposis excision. The bristle-like structure at the front ends of the actuator can prevent a captured object from escaping, and provide protection for the camera.
7. The robot front-end flexible actuator is made of flexible high-molecular polymer such as polyvinyl chloride and dielectric elastomers. The deformation capability of these materials is strong, and the strong self-adaptive capability to the appearance of the captured object is achieved.
8. The flexible tactile sensor is integrated on the inner surface of the robot front-end flexible actuator. The contact pressure with an enveloped object can be detected. The fusion of tactile information and camera visual information can provide feedback for the precise operation of the robot.
9. The robot body is manufactured by injection molding. The front-end actuator is manufactured through cutting and folding. The manufacturing process is simple, and the raw material cost is low.
10. The robot leads out signals through the conducting wires and signal wires in the middle channel of the main body, which can be controlled remotely. The control method is simple and reliable.

BRIEF DESCRIPTION OF FIGURES

The drawings constituting a part of the disclosure are intended to provide further understanding of the disclosure. Exemplary embodiments of the disclosure and their descriptions are used to explain the disclosure and are not to be construed as unduly limiting the disclosure. In the drawings.

Figure 1:
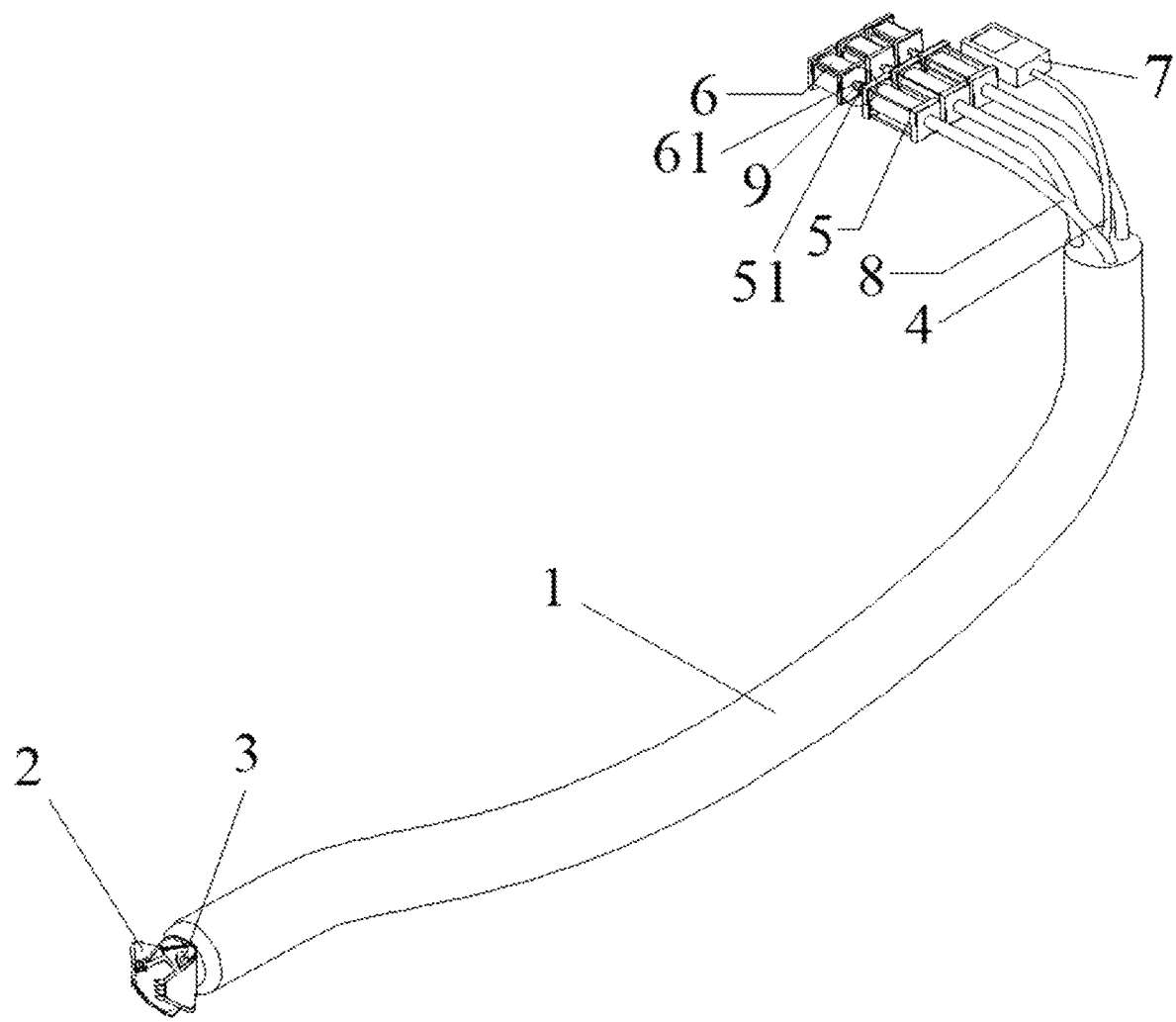
FIG. 1 is a schematic diagram of an integral structure of a diagnosis and treatment integrated soft medical robot for gastrointestinal endoscopy according to an embodiment of the disclosure.
Figure 2:
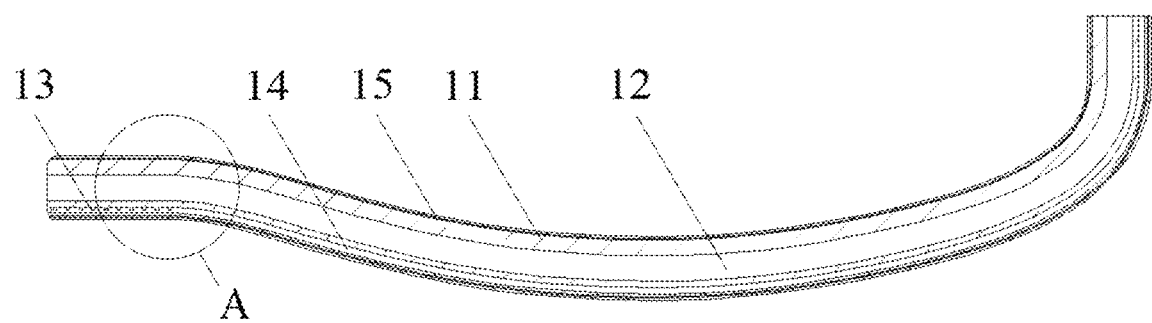
FIG. 2 is a sectional view of a robot body of the diagnosis and treatment integrated soft medical robot for gastrointestinal endoscopy according to an embodiment of the disclosure.
Figure 3:
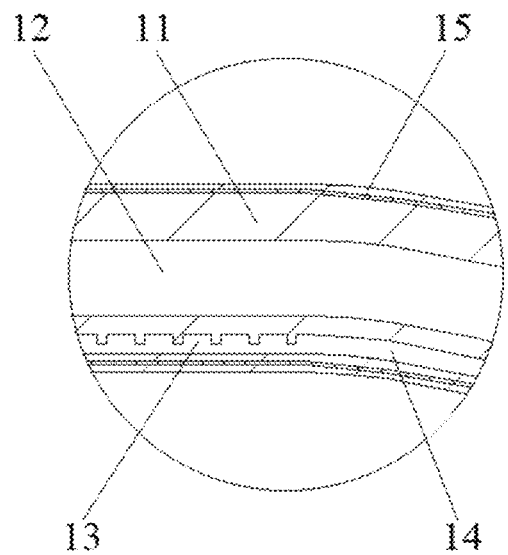
FIG. 3 is a schematic enlarged view of a local structure of the part A in FIG. 2.
Figure 4:
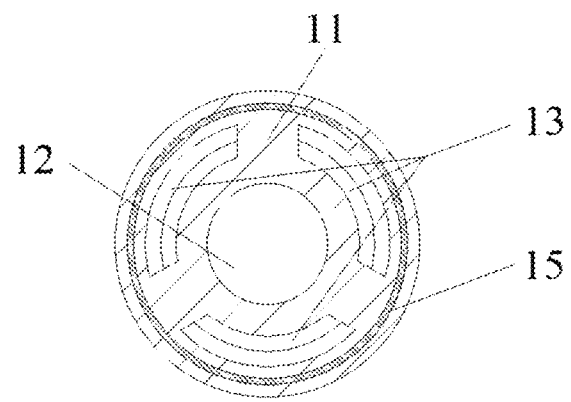
FIG. 4 is a sectional view of the robot body of the diagnosis and treatment integrated soft medical robot for gastrointestinal endoscopy in another perspective according to the embodiment of the disclosure.

In the figures:
1 denotes a robot body, 11 denotes a robot body silicone tube wall, 12 denotes a central channel, 13 denotes a robot body front-end lattice microfluid channel, 14 denotes a robot body smooth microfluid channel, 15 denotes a fiber woven mesh,
2 denotes a flexible dielectric elastomer actuator, 21 denotes a flexible dielectric elastomer actuator framework, 211 denotes a framework main body, 212 denotes a capture arm, 22 denotes a dielectric elastomer driving unit, 221 denotes a dielectric elastomer layer, 222 denotes a first flexible electrode layer, 223 denotes a first sensing layer, 224 denotes a first encapsulation protection layer, 225 denotes a second sensing layer, 226 denotes a second encapsulation protection layer, 227 denotes a second flexible electrode layer, 228 denotes a third encapsulation protection layer,
3 denotes a camera, 4 denotes a conducting wire and signal wire, 5 denotes an air cylinder, 6 denotes a linear motor, 7 denotes a controller, and 8 denotes an external hose.

DETAILED DESCRIPTION

It should be noted that embodiments of the disclosure and features in the embodiments may be combined with one another without conflict.

The disclosure will now be described in detail with reference to the drawings in combination with embodiments.

As shown in FIG. 1 to FIG. 7, a diagnosis and treatment integrated soft medical robot for gastrointestinal endoscopy is provided. This medical robot with a front-end actuator can acquire images, and can be used for digestive tract disease diagnosis and minimally invasive surgery. The diagnosis and treatment integrated soft medical robot for gastrointestinal endoscopy includes a robot body 1, a camera 3, illumination devices, a flexible dielectric elastomer actuator 2, air cylinders 5, linear motors 6, a controller 7 and external hoses 8. The robot body 1 is a multichannel hose, and includes a central channel 12 and circumferential channels, the central channel 12 is configured to accommodate conducting wires and signal wires 4. The circumferential channels include three microfluid channels. The front end of each microfluid channels is a sealed end, a rear end of each of the microfluid channels is an open end, and the open end of each of the microfluid channels communicates with an end opening of a flow channel of one air cylinder 5.

The camera 3 is disposed at a front end of the central channel 12 of the robot body, and a plurality of illumination devices are distributed around the camera 3.

The flexible dielectric elastomer actuator 2 is disposed at the front end of the robot body 1 and is fixedly connected to the front end of the robot body 1. The air cylinders 5, the linear motors 6 and the controller 7 are all disposed at a rear end of the robot body 1. Each microfluid channels is correspondingly disposed with one air cylinder. Each air cylinder corresponds to one linear motor. The microfluid channels and the air cylinder are connected through the external hose 8. The piston rod 51 of the air cylinders 5 is connected with a shaft 61 of the corresponding linear motor through a coupling 9. The conducting wires and signal wires 4 of the camera 3, the conducting wires and signal wires 4 of the flexible dielectric elastomer actuator 2 are all connected with the controller 7. The three linear motors 6 drive the piston rod 51 of the corresponding cylinder 5 to control the fluid pressure in the three microfluidic channels respectively, so that the robot body 1 can turn flexibly under the fluid drive. The camera 3 can perform all-around shooting on the inner wall of the digestive tract and monitor the state of the inner wall of the digestive tract in real time for a long period, and performs real-time image acquisition. The controller 7 controls the flexible dielectric elastomer actuator 2 to capture a target.

The three microfluid channels of the robot body 1 are uniformly distributed in a circumferential direction. The inner wall of a front section portion of each microfluid channels adopts lattice structures as robot body front end lattice microfluid channels 13 so as to ensure a more obvious bending angle of the front end. The inner wall of other portions of the microfluid channels is of a smooth structure as a robot body smooth microfluid channel 14. Under the condition of the same air pressure, the inner and outer wall stiffness difference caused by the lattice-shaped microfluid channels relative to the smooth wall is greater, so that the bending angle of the lattice-shaped microfluid positions is greater, and the bending effect is more obvious under the condition of the same driving air pressure. In this position, the effect of the smooth wall microfluid channels is mainly fluid conveyance. The effect of the lattice-shaped microfluid channels is mainly bending guiding. By adjusting the relative pressure difference of the fluid in the three microfluid channels, the 360° steering of the front end of the robot body can be achieved, so that the guiding in the digestive tract can be achieved. This way can provide convenience for the observation diagnosis of the camera and the operation of the front-end actuator.

Figure 5:
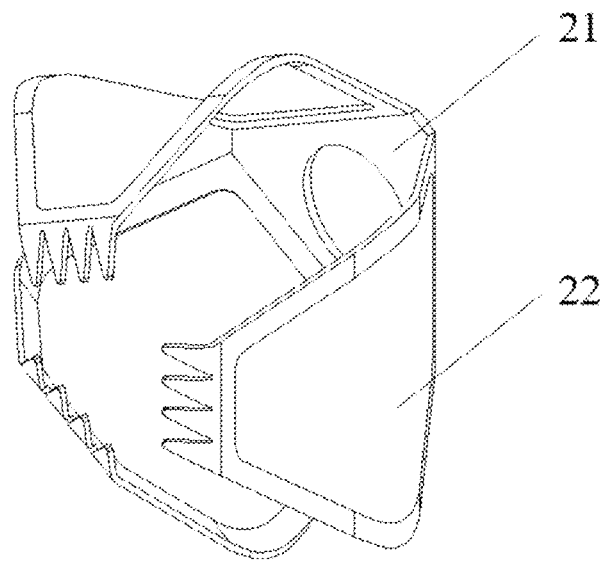
FIG. 5 is a schematic diagram of a stereoscopic structure of a front-end flexible dielectric elastomer actuator.
Figure 6:
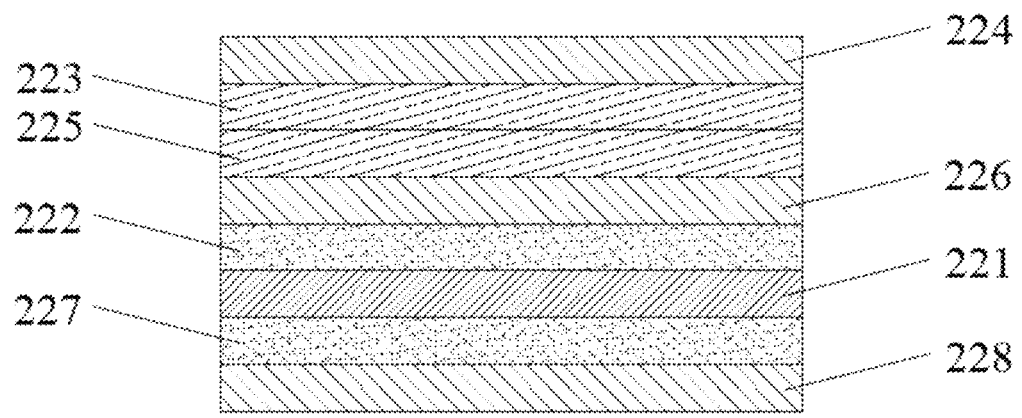
FIG. 6 is a schematic diagram of an interlayer structure of a front-end actuator dielectric elastomer driving unit.
Figure 7:
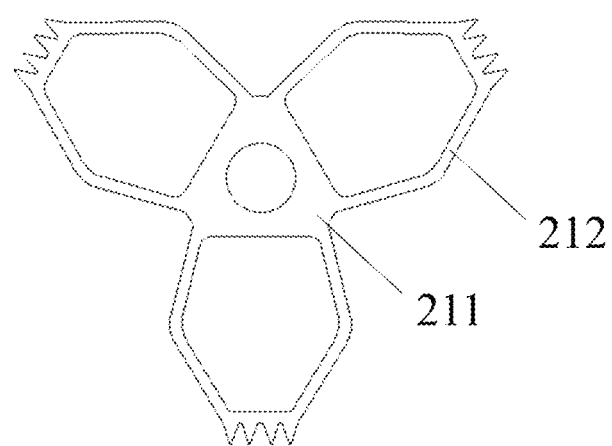
FIG. 7 is a schematic plan diagram of a front-end flexible actuator framework in an unfolded state.

The flexible dielectric elastomer actuator 2 includes a flexible dielectric elastomer actuator framework 21 and three dielectric elastomer driving units 22. The flexible dielectric elastomer actuator framework 21 includes a framework main body 211 and three capture arms 212. The three capture arms 212 are uniformly disposed on the periphery of the framework main body 211. one dielectric elastomer driving unit 22 is pasted to an inner side of each capture arms 212. The three capture arms 212 are folded to be in a gathered state. The dielectric elastomer driving units 22 includes a first encapsulation protection layer 224, a first sensing layer 223, a second sensing layer 225, a second encapsulation protection layer 226, a first flexible electrode layer 222, a dielectric elastomer layer 221, a second flexible electrode layer 227 and a third encapsulation protection layer 228 sequentially disposed from inside to outside. The first sensing layer 223, the second sensing layer 225, the first encapsulation protection layer 224 and the second encapsulation protection layer 226 are combined into form a flexible tactile sensor. The area of the dielectric elastomer layer 221 can be expanded or contracted by adjusting a driving voltage. The flexible dielectric elastomer actuator 2 is driven to complete an opening or closing action so as to achieve the capture on the target. The sensing layer can detect a contact pressure between the inner wall of the actuator and the captured object. The dielectric elastomer layer shows area expansion at a high voltage. By adjusting the driving voltage, the flexible dielectric elastomer actuator can complete opening and closing actions to achieve the capture on the gastrointestinal calculus, etc. When no driving voltage is applied, the pre-tightening force of the dielectric elastomer per se can keep the three capture arms 212 in a gathered state. According to the actual size of the captured gastrointestinal stones, the dielectric elastomer actuator can be opened or closed at an appropriate angle. FIG. 7 shows a plane structure of the flexible framework in the unfolded state. Through the attachment of the dielectric elastomer driving units and folding, the gathered state of the three capture arms 212 towards the center as shown in FIG. 5 is obtained.

The framework main body 211 is of a regular triangular structure. The center through hole allowing the camera 3 to pass and to be fixed is provided in the center of the framework main body 211. The capture arms 212 are of hexagonal structures. The capture arm 212 is a hexagonal structure, the middle of the capture arm 212 is provided with a hexagonal through hole. The dielectric elastomer driving units are pasted to the hexagonal through holes such that the three capture arms 212 can be conveniently folded into the gathered state. The dielectric elastomer driving units can drive the capture arms to achieve good deformation when it is powered on.

A layer of fiber woven mesh 15 is embedded in an outer layer of the robot body 1 so as to limit the radial and circumferential deformation of the robot body.

The bristle-like locking structures are provided at front ends of the capture arms 212. The front end of the capture arm 212 is provided with a bristle-like locking structure, which can effectively lock the captured object, prevent the captured object from escaping, and provide protection for the camera.

The sensing layer is made of carbon nano materials such as graphene, carbon nano tubes, etc. The surface of the sensing layer is provided with a micro-nano structure. The specific micro-nano structure can be semi-spherical, pyramid-shaped, cylindrical, conical or irregular-shaped bulges, etc. The sensing layer may adopt a single-layer or multi-layer structure. The sensing layer is preferably a thin film with a surface micro-nano structure that made of carbon nano material or metal nano material. The encapsulation protection layer uses a polydimethylsiloxane thin film. The material of the robot body 1 is preferably silicone rubber. The robot body silicone rubber tube wall 11 can adjust the robot body stiffness to a certain extent, protect internal circuits and reduce the influence of electronic elements on the digestive tract. The material of the flexible dielectric elastomer actuator framework 21 is preferably polyvinyl chloride.

A work process of the diagnosis and treatment integrated soft medical robot for gastrointestinal endoscopy of the disclosure is as follows:

After the front-end flexible dielectric elastomer actuator of the medical robot for gastrointestinal endoscopy enters the inside of the digestive tract, the three linear motors are respectively controlled to push the piston rods of the air cylinders, sealed cavities with the three fluid channels are located are extruded to generate different air pressures so as to achieve the bending guiding of the portion of the front end of the main body with the lattice microfluid channel. The robot body enters the inside of the digestive tract and extends through rear end delivery. In the robot body delivery process, the front-end camera can monitor the state of the inner wall of the digestive tract in real time. When the front-end flexible actuator reaches the lesion, the advancing and retreating of the front-end flexible actuator can be realized by adjusting the delivery length of the rear end of the robot body. At the same time, the driving voltage of the dielectric elastomer actuator can also be adjusted, that is, the opening and closing action of the dielectric elastomer actuator can be realized by increasing or decreasing the driving voltage respectively. The dielectric elastomer actuator can be sequentially driven to complete the opening, capture, closing and locking actions, so the capture on the gastrointestinal calculus can be realized. In the diagnosis and treatment process, the tactile information acquired by the tactile sensor at the inner wall of the dielectric elastomer actuator can be fused with the visual information acquired by the camera so as to judge whether the gastrointestinal calculus inside the flexible dielectric elastomer actuator is tightly grasped or not, the specific position and motion state. Through this design, the precision operation and rapidity of the robot can be guaranteed, and the injury to the inner wall of the digestive tract can be possibly reduced.

The soft medical robot for gastrointestinal endoscopy of the disclosure is used for the diagnosis and treatment of diseases such as gastrointestinal calculus. At the same time, due to its characteristics of high freedom degree, high operation precision, full soft material assemblies and the like, the application prospects in the fields of thrombectomy, hydraulic equipment pipeline clearing and the like are also shown.

The descriptions above are only exemplary embodiments of the disclosure and are not intended to limit the disclosure. Any modifications, equivalent replacements, improvements and the like made within the spirit and principle of the disclosure shall fall within the protection scope of the disclosure.

What is claimed is:

1. A diagnosis and treatment integrated soft medical robot for gastrointestinal endoscopy, comprising: a robot body (1), a camera (3), illumination devices, a flexible dielectric elastomer actuator (2), air cylinders (5), linear motors (6), a controller (7) and external hoses (8), wherein the robot body (1) is a multichannel hose, and comprises a central channel (12) and circumferential channels; the central channel (12) is configured to accommodate conducting wires and signal wires (4); the circumferential channels comprise at least three microfluid channels; a front end of each of the microfluid channels is a sealed end; a rear end of each of the microfluid channels is an open end; and the open end of each of the microfluid channels is communicated with a flow channel port of an air cylinder (5);

the camera (3) is disposed at a front end of the central channel (12) of the robot body, and a plurality of illumination devices are distributed around the camera (3);

the flexible dielectric elastomer actuator (2) is disposed at a front end of the robot body (1) and is fixedly connected to the front end of the robot body (1); the air cylinders (5), the linear motors (6) and the controller (7) are all disposed at a rear end of the robot body (1); each of the microfluid channels is correspondingly disposed with one air cylinder; each of the air cylinders corresponds to one linear motor; the microfluid channels and the corresponding air cylinders are connected through the external hoses (8); a piston rod (51) of the air cylinder (5) is connected with a shaft (61) of the corresponding linear motor through a coupling (9), and conducting wires and signal wires (4) of the camera (3) and conducting wires and signal wires (4) of the flexible dielectric elastomer actuator (2) are all connected with the controller (7); the linear motors (6) drive the piston rods (51) of the corresponding cylinders (5) to control a fluid pressure in the three microfluidic channels, respectively, so that the robot body (1) can turn flexibly under a fluid drive; and the camera (3) performs real-time image acquisition, and the controller (7) controls the flexible dielectric elastomer actuator (2) to capture a target;

and wherein the flexible dielectric elastomer actuator (2) comprises a flexible dielectric elastomer actuator framework (21) and three dielectric elastomer driving units (22); the flexible dielectric elastomer actuator framework (21) comprises a framework main body (211) and three capture arms (212); the three capture arms (212) are uniformly disposed on the periphery of the framework main body (211), and one dielectric elastomer driving unit (22) is pasted to an inner side of each of the capture arms (212); the three capture arms (212) are folded to be in a gathered state; the dielectric elastomer driving units (22) comprise a first encapsulation protection layer (224), a first sensing layer (223), a second sensing layer (225), a second encapsulation protection layer (226), a first flexible electrode layer (222), a dielectric elastomer layer (221), a second flexible electrode layer (227) and a third encapsulation protection layer (228) sequentially disposed from inside to outside; and an area of the dielectric elastomer layer (221) can be expanded or contracted by adjusting a driving voltage, so that the flexible dielectric elastomer actuator (2) can be driven to complete an opening or closing action, so as to capture the target.

2. The diagnosis and treatment integrated soft medical robot for gastrointestinal endoscopy according to claim 1, wherein the robot body (1) comprises the three microfluid channels, the three microfluid channels are uniformly distributed in a circumferential direction; an inner wall of a front section portion of each of the microfluid channels adopts lattice structures as robot body front end lattice microfluid channels (13); and an inner wall of other portions of the microfluid channels is of a smooth structure as a robot body smooth microfluid channel (14).

3. The diagnosis and treatment integrated soft medical robot for gastrointestinal endoscopy according to claim 1, wherein the framework main body (211) is of a regular triangular structure; a center through hole allowing the camera (3) to pass and to be fixed is provided in a center of the framework main body (211); and capture arms (212) are of a hexagonal structure, and a middle of the capture arm (212) is provided with a hexagonal through hole.

4. The diagnosis and treatment integrated soft medical robot for gastrointestinal endoscopy according to claim 3, wherein bristle-like locking structures are provided at front ends of the capture arms (212).

5. The diagnosis and treatment integrated soft medical robot for gastrointestinal endoscopy according to claim 1, wherein a layer of fiber woven mesh (15) is embedded in an outer layer of the robot body (1).

6. The diagnosis and treatment integrated soft medical robot for gastrointestinal endoscopy according to claim 1, wherein the first sensing layer (223), the second sensing layer (225), the first encapsulation protection layer (224) and the second encapsulation protection layer (226) are combined into a flexible tactile sensor.

7. The diagnosis and treatment integrated soft medical robot for gastrointestinal endoscopy according to claim 6, wherein a sensing layer is a thin film with a surface micro-nano structure made of carbon nano material or metal nano material.

8. The diagnosis and treatment integrated soft medical robot for gastrointestinal endoscopy according to claim 1, wherein a material of the encapsulation protection layer is a polydimethylsiloxane thin film.

9. The diagnosis and treatment integrated soft medical robot for gastrointestinal endoscopy according to claim 1, wherein a material of the robot body (1) is silicone rubber, and a material of the flexible dielectric elastomer actuator framework (21) is polyvinyl chloride.

\* \* \* \* \*